United States Patent [19]

Alexander

[11] Patent Number: 5,496,283

[45] Date of Patent: Mar. 5, 1996

[54] APPARATUS FOR SECURING INTRAVENOUS OR INTRACAVITY MEDICAL TUBING

[75] Inventor: Gary E. Alexander, Baton Rouge, La.

[73] Assignee: Medisys Technologies, Inc., Baton Rouge, La.

[21] Appl. No.: 282,529

[22] Filed: Jul. 28, 1994

[51] Int. Cl.⁶ .................................................. A61M 25/02
[52] U.S. Cl. ........................ 604/180; 128/DIG. 26
[58] Field of Search .......................... 604/174, 177, 604/179, 180; 128/DIG. 26

[56] References Cited

U.S. PATENT DOCUMENTS

| | | | |
|---|---|---|---|
| 3,046,984 | 7/1962 | Eby | 604/180 |
| 3,568,679 | 3/1971 | Reif | 128/DIG. 26 |
| 3,826,254 | 7/1974 | Mellor | 604/180 |
| 3,834,380 | 9/1974 | Boyd | 604/180 |
| 4,122,857 | 10/1978 | Haerr | 604/188 |
| 4,316,461 | 2/1982 | Marais et al. | 604/179 |
| 4,333,468 | 6/1982 | Geist | 604/180 |
| 4,435,174 | 3/1984 | Redmond | 604/174 |
| 4,704,177 | 11/1987 | Vaillancourt | 604/180 |
| 4,711,636 | 12/1987 | Bierman | 604/180 |
| 4,820,282 | 4/1989 | Hogan | 128/DIG. 28 |
| 5,112,312 | 5/1992 | Luther | 128/DIG. 26 |

*Primary Examiner*—Paul J. Hirsch
*Attorney, Agent, or Firm*—Roy, Kiesel & Tucker

[57] ABSTRACT

This invention relates to an apparatus for preventing tug trauma to a patient's skin caused by movement of a tube having an insertion means which may be inserted into the patient's skin, comprising a member having a first side and a second side, a retaining structure affixed to the first side, the retaining structure having a cylindrical-shaped passageway extending through the retaining structure, the passageway having an entry opening positioned at about a center section of the first side and shaped to receive the tube and having an exit opening positioned toward a first perimeter section of the first side and shaped to permit the tube to exit the passageway, the passageway having a diameter shaped to restrict movement of the tube through the passageway so that the entry opening becomes a center of rotation of the member when a lateral force would be placed on a section of the tube extending past the entry opening, and the second side containing an adhesive means to adhere the member to the patient's skin.

7 Claims, 3 Drawing Sheets

APPARATUS FOR SECURING INTRAVENOUS OR INTRACAVITY MEDICAL TUBING

BACKGROUND OF THE INVENTION

This invention relates to an apparatus and method of securing an intravascular or catheter tubing to a patient. More particularly, but not by way of limitation, this invention relates to an apparatus and method of eliminating tug trauma to a catheter site or intravascular therapy site on a patient.

Many times, a medical patient will require various types of treatments which require the use of intravascular (intravenous) or intracavity tubes in order to introduce fluids into the body or to drain fluids from the body. When this is done, a catheter tube, or needle with tube attached, is utilized in order to provide a medium for the fluid to flow into or from the body. The catheter or needle and the fluid source are fluidly connected by means of a tube, variously referred to as a catheter tube, intravenous tube, or medical tube.

The needle or catheter, therefor, is inserted into the body at the appropriate intravenous therapy or catheter site. Further, due to the different types of medical treatments, the catheter or intravenous needle may be required to remain in the site for long periods of time. It is therefore desirable that the catheter or intravenous needle be protected in order to prevent dislodging due to inadvertent or accidental tugging on the catheter or intravenous tubing.

Inadvertent or accidental tugging on the catheter or intravenous tubing often leads to site problems. In the case of an intravenous needle, such tugging can cause patient discomfort, fluid flow blockage, injury or perforation of the vein wall (the lume), site irritation and inflammation with sepsis, dislodgement of the needle, and infiltration of the introduced fluid into surrounding muscular tissue. In the case of an intracavity drainage catheter, such tugging can cause dislodgement of the catheter, fluid flow blockage, internal and site sepsis, and patient discomfort. In each case, if the site is not adequately protected from such tugging, serious medical complications can result.

At present, the most commonly used method of attempting to protect these sites from accidental or inadvertent tug trauma is to tape the tubing to a patient's body a few inches away from the intravenous needle or intracavity catheter site. Sometimes the tubing is taped to the body in more than one place. With time and repeated patient movement, tugs on the tubing frequently cause the tape to lose its adhesive grip on the tubing, even though it may retain its grip on the patient's skin. This permits the tugging, in increasing degrees as the tape fails to grip the tubing, to be transmitted to the intravenous needle or intracavity catheter site with resultant hazardous and unsafe conditions, particularly if the patient is in a critical medical condition.

In U.S. Pat. No. 4,966,590 to Kalt, the patent discloses an IV Clamp With Membrane Dressing wherein a first and second clamp is utilized for holding an article to an object. In U.S. Pat. No. 4,170,995 to Levine a Catheter Clamp is disclosed. The patent claims a holder for clamping in place a catheter on a patient's body, which holder includes a pliant adhesive-bearing base which is adhered to the patient's skin.

A Catheter Retention Device And Method is disclosed in U.S. Pat. No. 4,699,616 to Nowak et al. In particular, this patent describes a device for retaining a catheter in place at its point of entry into the patient's body. Another type of device is seen in U.S. Pat. No. 3,782,388 to Page regarding a Medical Tube Holder. This patent describes an article for attaching a medical tube to the body of a patient. Also, see U.S. Pat. No. 4,898,587 to Mera involving an Intravenous Line Stabilizing Device. The invention describes a device for affixing a medical tube to a part of a body. In U.S. Pat. No. 4,698,057 to Joishy the inventor claims a Built-In Assembly For Stabilizing And Securing Intravascular Needle Or Catheter Like Device.

In addition, Dow Corning has offered for sale a suprapubic drainage system under the brand name SILASTIC® CYSTOPATH which contains as one of its elements a circular disc having a tube retaining member extending across the disc diameter and provided with an opening in the member extending vertically through the disc for receiving a catheter.

Despite these numerous inventions, none of the above apparatus presents a simple, easily constructed, and easily adaptable device which effectively prevents tug trauma to a catheter or intravenous needle site. In addition, some of these prior art devices are either too complicated, or lack simplicity in design and make the use and manufacture cost prohibitive. Therefore, it is an object of this invention to have a device which efficiently prevents tug trauma to a catheter or intravenous needle site caused either by medical personnel movement of peripheral equipment, or alternatively, patient movement.

SUMMARY OF THE INVENTION

An advantage of the present invention includes the ability of having tubing slack between the catheter or intravenous needle site and the circular member. Another advantage is that the entry point serves to transfer any trauma caused from forceful movement of the tube to the circular member. Still another advantage includes that the apparatus requires little training of the medical personnel involved with its application and use.

Yet another advantage is that the invention may be manufactured at low cost. Still another advantage lies in the fact that the procedure for replacing the apparatus with a new apparatus or repositioning the apparatus is uncomplicated and easily performed.

Other advantages and objects of this invention will become apparent from the ensuing descriptions of the invention.

Accordingly, an apparatus for preventing tug trauma to a patient's skin caused by movement of a tube having an insertion means which may be inserted into the patient's skin, comprising a member having a first side and a second side, a retaining structure affixed to the first side, the retaining structure having a cylindrical-shaped passageway extending through the retaining structure, the passageway having an entry opening positioned at about a center area of the first side and shaped to receive the tube and having an exit opening positioned toward a first perimeter area of the first side and shaped to permit the tube to exit the passageway, the passageway having a diameter shaped to restrict movement of the tube through the passageway so that the entry opening becomes a center of rotation of the member when a lateral force would be placed on a section of the tube extending past the entry opening, and the second side containing an adhesive means to adhere the member to the patient's skin.

DESCRIPTION OF THE PREFERRED EMBODIMENTS

Figure 1:
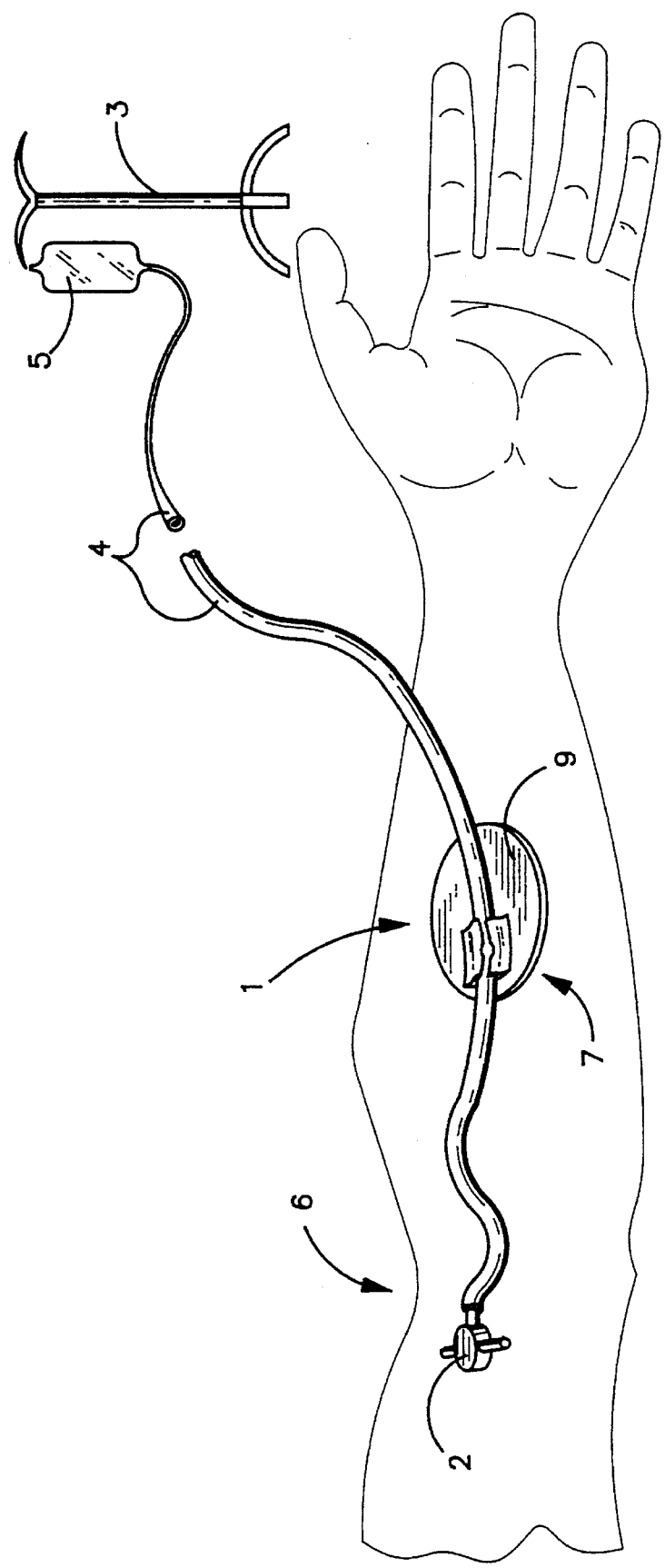
FIG. 1 is a perspective view of the invention as applied to the skin of the patient.

FIG. 1 depicts a conventional arrangement when a preferred embodiment of the securing member 1 is used in conjunction with an intravenous fluid injection procedure. In this arrangement needle 2 is fluidly connected by means of plastic tubing 4 to a fluid source, such as fluid bag 5. The needle 2 is inserted into a vein in a patient's arm 6. The area of insertion is commonly referred to as the intravenous needle site. It is also typical for a stand 3 to be provided to support fluid bag 5 at a height above the intravenous needle site to facilitate the flow of fluids from fluid bag 5 to needle 2 and into the patient's vein.

Figure 2:
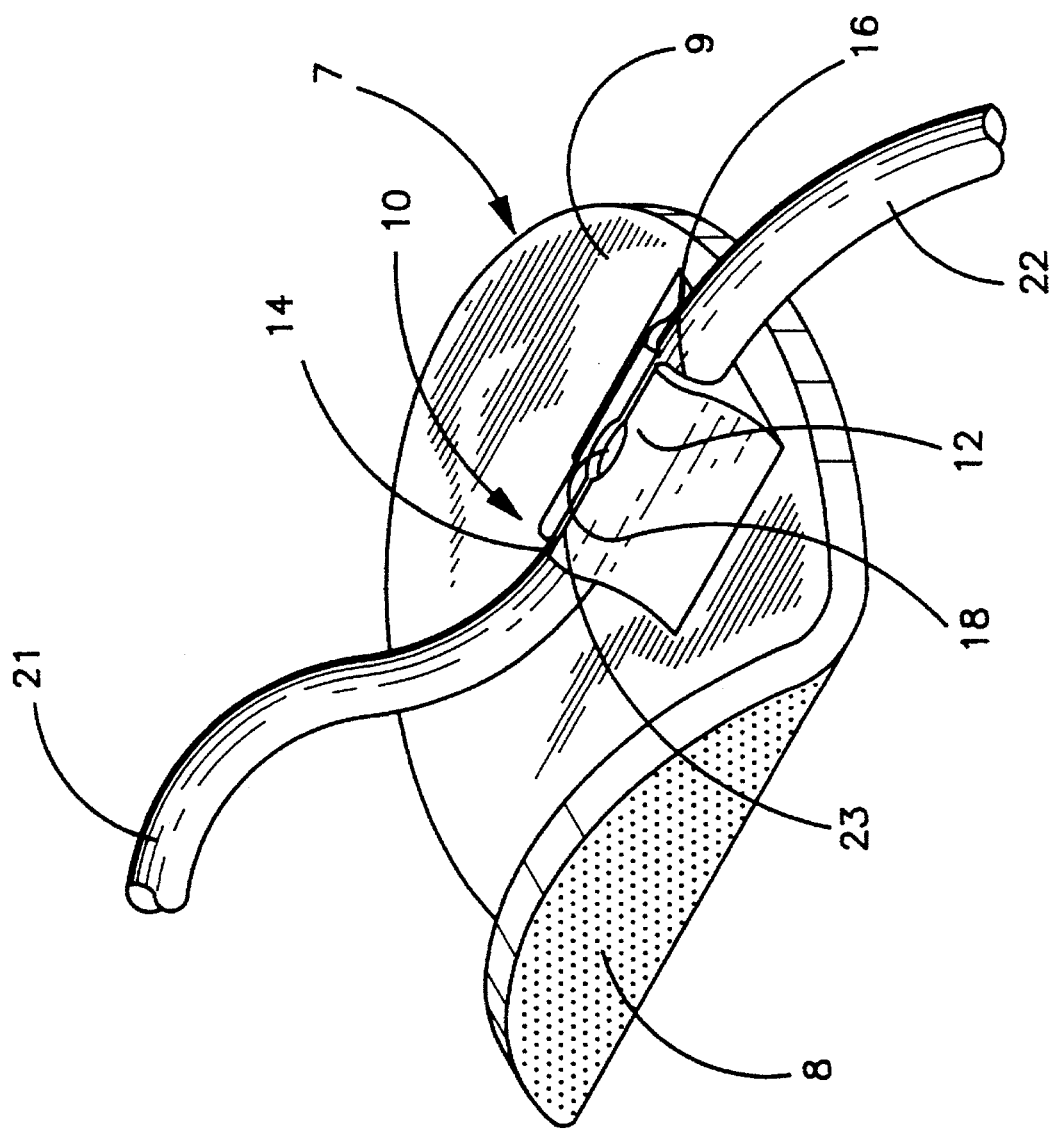
FIG. 2 is a perspective view of the invention.
Figure 3:
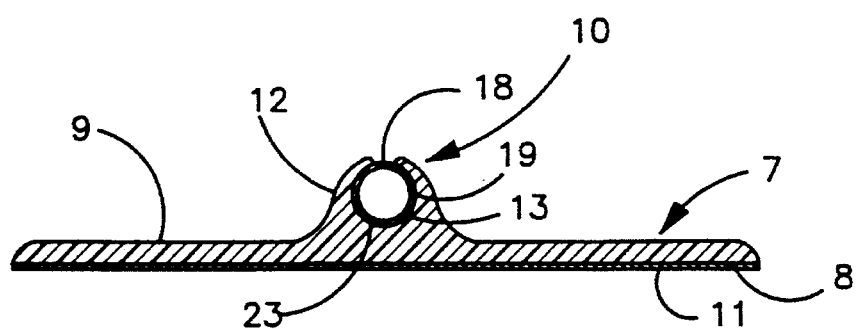
FIG. 3 is a cross-sectional area of the invention taken along line A—A of FIG. 2.

Referring to FIGS. 2 and 3, securing member 1 comprises a circular disc member 7 having a first side 8 having an adhesive composition applied thereto and a second side 9 to which is affixed a tube retaining structure 10. In a more preferred embodiment, a removable covering 11 will be affixed to the adhesive composition which can be peeled away to expose the adhesive composition when the securing member 1 is ready for use. Adhesive compositions typically used with surgical tape or adhesive bandages would be suitable.

It is preferred that disc member 7 be constructed of a pliable plastic or rubber material which will readily conform to the shape of the arm or other body member to which it will be secured. More preferably, disc member 7 will be constructed from material which is sufficiently clear to allow a person to determine if any rash develops on the skin area under the disc member 7.

Tube retaining structure 10 comprises a shoulder structure 12 affixed to side 9 and which extends above side 9 beginning at one end at about a perimeter section of disc member 7 and extending to the center section of disc member 7. In a preferred embodiment shoulder structure 12 and disc member 7 will be formed from a common molded piece of material. A passageway 13 extends through shoulder structure 12 being at entry opening 14, preferably in one end 15 located at the center section of disc member 7, and ending at exit opening 16, preferably at the opposite end 17 of shoulder structure 12 located at a periphery section of disc member 7. It is preferred that passageway 13 have a cross-sectional area shaped similar to that of tubing 4. It also preferred that the cross-sectional area be slightly less than that of tubing 4 to facilitate securing tubing 4 in a position relative to disc member 7.

Shoulder structure 12 is also provided with a slit 18 that extends along the length of and parallel with passageway 13 to facilitate tubing 4 being slipped into passageway 13. It is also preferred that shoulder structure 12 be formed of a pliable and elastic material that will allow the width of slit 18 to be increased to facilitate the placing of tubing 4 into passageway 13 and then return to its original width causing the walls 19 forming passageway 13 to contact tubing 4. Slit 18 may be positioned either at the top of shoulder structure 12 as shown in FIG. 3 or along the side of shoulder structure 12.

In another embodiment, walls 19 form a section 20 of passageway 13 whose centerline is arcuate in shape. Although it is slightly more difficult to insert tubing 4 into passageway 13 with this shape, greater gripping force can be provided to tubing 4 by walls 19 to prevent tubing 4 from being moved once it is positioned in passageway 13.

Figure 4:
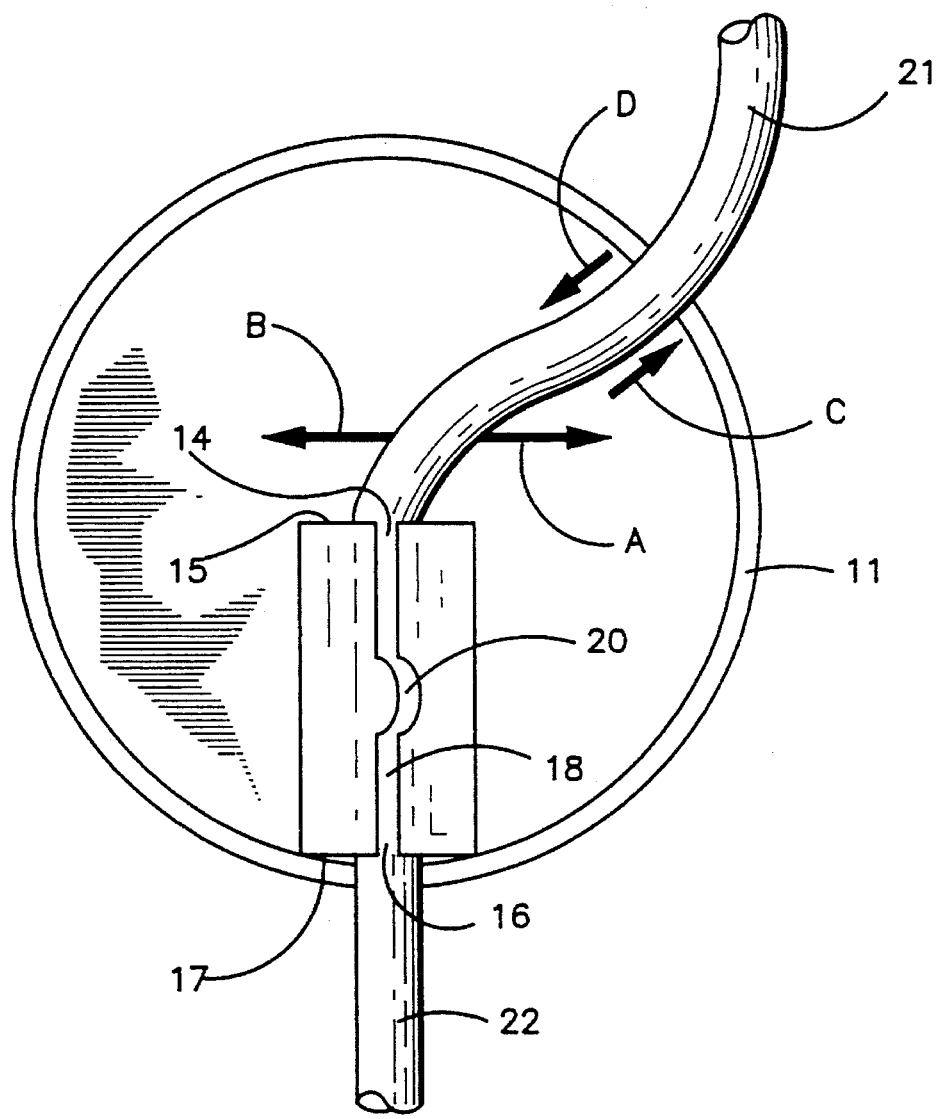
FIG. 4 is a perspective view illustrating some of the various movement associated with the invention.

Referring to FIGS. 1 and 4, it is seen that the disc member 7 offers significant advantages over conventional taping and other methods for securing catheters, intracavity medical tubing, or other similar devices. The most common tug trauma results from that section 21 of tubing 4 that extends from the taped area on the patient's body to the fluid bag 5. This can be caused by the patient moving his arms or rolling over on tubing section 21. This can cause substantial torquing or twisting forces to be placed at the taped site. To insure that these forces do not cause trauma at the intravenous needle site it is common to apply substantial tape about tubing 4 in order to secure it to the patient's body. When utilizing the securing member 1, tubing 4 is fixed within passageway 13 so that tubing section 21 extends from entry opening 14 to fluid bag 5. Because entry opening 14 is located at the center section of disc member 7, any forces applied to tubing 4 as shown by the directional arrows A–D are substantially less likely to pull securing member 1 from the patient's skin because there is more adhesive surface that must be lifted, than if entry opening 14 were located near the periphery of disc member 7.

Directional arrow A represents lateral movement of tubing section 21 in a clockwise rotation caused by some force. This force can be, for instance, movement of tubing section 21 by medical personnel. Tubing section 21 will move until it pivots about entry opening 14. This pivoting movement transfers the forces to end 15 of shoulder structure 12. If a substantial force is applied to tubing 4 in a clockwise direction, any further movement will be absorbed by end 15 and continued application of force will then be transferred to disc member 7 which may cause disc member 7 to rotate slightly on the patient's skin. However, the adhesive side 8 being attached to the patient's skin causes the rotation to be about the center section of disc member 7.

Likewise, if tubing section 21 is moved in a counterclockwise direction as illustrated by directional arrow B, then the forces will again be transferred to end 15. It is noted that the rotation resulting from these forces which may occur to disc member 7 will cause some movement in that section 22 of tubing 4 extending from exit opening 16 to needle 2. For this reason it is preferred that there be some slack in tubing section 22 to prevent any tug trauma to the intravenous needle site.

Directional arrow C depicts movement of tubing section 21 in the longitudinal direction, such as may be caused by a pulling on tubing 4. In this case the friction created by passageway walls 19 against that section 23 of tubing 4 absorb these longitudinal forces preventing tubing section 23 from moving. In still another embodiment passageway 13 may have a cross-section of varying diameters wherein at least one of the cross-sectional areas is less than the cross-sectional area of tubing section 23.

If tubing section 21 is subjected to a compressional force as illustrated by directional arrow D, then most of the compressional force should also be similarly absorbed.

Although it is preferred that side 8 be generally circular in shape, side 8 can still perform its function if it is rectangular, oblong, triangular or some other shape which permits sufficient adhesive surface to exist from entry opening 14 to the periphery of disc member 7 to prevent securing member 1 from being pulled off of the patient's body by normal tug trauma. A distance of about at least one inch from the entry opening 14 to the closest periphery point has been found to provide sufficient adhesive surface when using conventional adhesives.

In another alternate embodiment, adhesive may be applied to walls 19 to ensure that tubing 4 is affixed to tube retaining structure 10.

There are of course other obvious embodiments of the invention which are intended to be included within the scope of the claims set forth below.

What I claim is:

1. A system for preventing tug trauma to a patient's skin, comprising:
   (a) tubing having a first and second end,
   (b) means capable of being inserted into said patient's skin operatively attached to said first end of said tubing, and
   (b) a member comprising:
      (i) opposing first and second sides whose adjacent edges form a perimeter section of said member,
      (ii) a tubing retaining structure affixed to said first side, said tubing retaining structure having interior walls forming a passageway extending end-to-end through said tubing retaining structure, said passageway having an entry opening positioned at about a center section of said first side and shaped to receive said tubing and said passageway having an exit opening positioned adjacent said perimeter section and shaped to permit said tubing to exit said passageway, said passageway sized to receive said tubing and shaped to restrict movement of said tubing through said passageway, wherein said tubing is positioned in said passageway having said first end extending from said exit opening and said second end extending from said entry opening of said passageway, such that said entry opening becomes a center of rotation of said member when a lateral force would be placed on a section of said tubing extending past said entry opening; and
      (iii) said second side containing an adhesive means to adhere said member to said patient's skin.

2. The system according to claim 1 wherein a section of said walls are shaped to form said passageway having a section whose centerline is arcuate in shape.

3. The system according to claim 1 wherein said entry opening is less than about one inch from said perimeter section of said member.

4. The system according to claim 1 wherein said member is solid.

5. The system according to claim 1 wherein said adhesive means comprises an adhesive affixed to said second side and a covering extending over said adhesive and removably attached to said adhesive for removal when said device is to be used.

6. The system according to claim 1 wherein said tubing is positioned in said retaining structure such that said tubing extends from said entry opening and beyond said first side of said member.

7. The system according to claim 1 wherein said tube retaining structure is positioned to permit said tubing to extend unencumbered in a straight line from said entry opening across said first side of said member.

* * * * *